United States Patent [19]
Broderick et al.

[11] Patent Number: 5,939,387
[45] Date of Patent: Aug. 17, 1999

[54] METHOD OF TREATING INSULIN RESISTANCE

[75] Inventors: Carol Lynn Broderick, Monrovia; Richard Dennis DiMarchi, Carmel; Mark Louis Heiman; Lawrence Edward Stramm, both of Indianapolis, all of Ind.

[73] Assignee: Eli Lilly and Company, Indianapolis, Ind.

[21] Appl. No.: 08/708,620

[22] Filed: Sep. 5, 1996

Related U.S. Application Data

[60] Provisional application No. 60/003,473, Sep. 8, 1995.

[51] Int. Cl.$^6$ .......................... A61K 38/00; A61K 39/395
[52] U.S. Cl. .......................... 514/12; 424/130.1; 530/300
[58] Field of Search .......................... 514/12; 424/130.1; 530/300

[56] References Cited

U.S. PATENT DOCUMENTS

| | | | |
|---|---|---|---|
| 4,988,675 | 1/1991 | Froesch et al. | 514/4 |
| 5,093,317 | 3/1992 | Lewis et al. | 514/12 |
| 5,126,324 | 6/1992 | Clark et al. | 514/12 |
| 5,187,151 | 2/1993 | Clark et al. | 514/3 |

FOREIGN PATENT DOCUMENTS 0 511 003 A1  10/1992  European Pat. Off. .

OTHER PUBLICATIONS

Gregon'adis,G. et al. 1993. Trends in Biotech 11:440–442.
Richards,NT. 1984. Diabetologia, 27: 529–534.
Martina, V. et al. 1995. Horm. Metab. Res. 27:26–30.
Rudman et al., 1990 *New Eng. J. Med.*, 323(1):1–6.
Salomon et al. 1989, *New Eng. J. Med.*, 321(26):1797–1803.
Marcus et al., 1990 *J. Clin. End. Met.*, 70(2):519–527.
Jorgensen et al., 1989, *Lancet*, Jun. 3:1221–1225.
Binnerts et al., 1988, *J. Clin. End. Met.*, 67(6):1312–1316.
Hammerman, M.R., 1987, *Endocrin. Meta. Clin.*, 16(4):995–1011.
Rudman et al., 1987, *Gerontology*, 33:307–314.
Dietz et al., 1986, *Am. J. Clin. Nutr.*, 43(4):696.
Rudman, D., 1985, *J. Am. Ger. Soc.*, 33(11):800–807.
Sonntag et al., 1985, *J. Gerontol.*, 40(6):689–694.
Rudman et al., 1981, *J. Clin.Invest.*, 67;1361–1369.
Johanson et al., 1981, *Johns Hopkins Med. J.*, 149:115–117.
Root et al., 1969, *J. Gerontol.*, 24:97–103.
Clark et al., 1996, 10th International Congress of Endocrinology, Abstracts, No. P1–591.
Bowers, C.Y., *J. Pediatr. Endocrin.*,6(1), pp. 21–31, 1993.
Rizza, et al., *Diabetes*, vol. 31, pp. 663–669, Aug. 1982.
Giustina et al., *TEM*, vol. 5, No. 1, pp. 73–78, 1994.
Rosenfeld et al., *J. of Clin. Endo. and Metab.*, vol. 54, No. 5, pp. 1033–1038, 1982.
Davidson, M. B., *Endocrine Reviews*, vol. 8, No. 2, pp. 115–131, 1987.
Thorner, M.O., *Acta Paediatr Suppl.* 388:2–7, 1993.
Frohman et al., *Endocrine Reviews*, vol. 7, No. 3, pp. 223–253, 1986.
Diequez et al., TEM vol. 6, No. 2, pp. 55–59, 1995.
Johansson, et al., Metabolism, vol. 45(3), 1996:pp. 362–369.

*Primary Examiner*—Sheela Huff
*Assistant Examiner*—Yvonne Eyler
*Attorney, Agent, or Firm*—Robert S. Maciak; Steven P. Caltrider

[57] ABSTRACT

The present invention is in the field of human medicine, particularly in the treatment of Non-insulin Dependent Diabetes Mellitus (NIDDM) and other insulin resistant states such as those associated with obesity and aging. The invention provides a method of treating insulin resistant mammals, which comprises administering to a mammal in need thereof a growth hormone releasing agent.

22 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 44 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
35                  40

(2) INFORMATION FOR SEQ ID NO:2:

(i) SEQUENCE CHARACTERISTICS:
       (A) LENGTH: 29 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Xaa Ala Asp Ala Ile Phe Thr Xaa Xaa Tyr Arg Lys Val Leu Xaa Gln
1               5                   10                  15

Leu Ser Ala Arg Lys Xaa Leu Gln Xaa Ile Xaa Ser Arg
            20                  25

(2) INFORMATION FOR SEQ ID NO:3:

(i) SEQUENCE CHARACTERISTICS:
       (A) LENGTH: 32 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

Gly Arg Gln Val Asp Ser Leu Trp Ala Asp Gln Arg Gln Leu Ala Leu
1               5                   10                  15

Glu Ser Ile Leu Ala Thr Leu Leu Gln Glu His Arg Asn Ser Gln Gly
            20                  25                  30

(2) INFORMATION FOR SEQ ID NO:4:

(i) SEQUENCE CHARACTERISTICS:
       (A) LENGTH: 32 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:4:

```
Gly Arg Gln Val Asp Gly Val Trp Thr Asp Gln Gln Gln Leu Ala Leu
1             5                   10                  15

Glu Ser Thr Leu Val Ser Leu Leu Gln Glu Arg Arg Asn Ser Gln Gly
        20              25              30
```

METHOD OF TREATING INSULIN RESISTANCE

This application is a continuation of U.S. provisional application No. 60/003,473, filed Sep. 8, 1995.

FIELD OF THE INVENTION

The present invention is in the field of human medicine, particularly in the treatment of Non-Insulin Dependent Diabetes Mellitus (NIDDM) and other insulin resistant states such as those associated with obesity and aging.

BACKGROUND OF THE INVENTION

In 1930 Houssay and Biasotti demonstrated in dog that removal of the anterior pituitary ameliorates the diabetic symptoms (hyperglycemia, glycosuria, ketonuria) resulting from previous pancreatectomy. Houssay, B. A. et al., *Compt. Rend. Soc. Biol.* 104:407 (1930). Houssay continued these studies by injecting pituitary extract into the hypophysectomized, pancreatectomized dog and reported that the improvement in the diabetic condition was abolished. Houssay, B. A. et al., *N. Enal. J. Med.* 214:961 (1936). Houssay speculated that the primary pituitary factor for this anti-insulin-like action was growth hormone (GH). More recently, these studies have been confirmed in normal dogs. Indeed, when GH was administered for 32 to 44 days the treatment caused a profound insulin antagonism that initially resulted in increased insulin secretion accompanied by elevated fasting plasma glucose (increased insulin resistance) with eventual exhaustion of the pancreatic β-cell and development of permanent diabetes. Pierluissi, J. et al., *Diabetologia* 18: 223 (1980).

Diabetogenic actions of GH have also been reported in human. Several studies have examined insulin sensitivity in acromegalic patients. Glucose utilization and suppression of hepatic glucose production was impaired during euglycemic clamps. Hansen, I. et al., *Am. J. Physiol.* 250:E269 (1986). Forearm muscle glucose uptake after insulin infusion was also decreased in acromegalics. Galbraith, H. et al., *Diabetes* 9:459 (1960). Impaired glucose tolerance and hyperinsulinemia were reversed by either pituitary surgery, Levin, S. R. et al., *Am. J. Med.* 57:526 (1974), or bromocriptine therapy, Feek, C. M. et al., *J. Clin. Endocrinol.* 22:532 (1981). As in acromegalic patients, GH administration to normal volunteers resulted in impaired suppression of hepatic glucose production, decrease glucose utilization, and insulin resistance. Rizza, R. A. et al., *Diabetes* 31:663 (1982); Bratusch-Marrain, P. R. et al., *J. Clin. Endocrinol. Metab.* 55:973 (1982) and Fineberg, S. E. et al., *Diabetes* 23:499 (1974). Because human GH is now readily available, there is increased potential to use it to treat conditions other than GH-deficient children. Recently, Sharp, Beshyah and Johnston, Sharp, P. S. et al., *Bailliere Clin. Endo.* 6:819 (1992), have warned that when considering such therapies one also need consider iatrogenic secondary diabetes.

These anti-insulin actions of GH aggravate the metabolic problems of patients with insulin dependent diabetes mellitus (IDDM) or Type I diabetes since GH is elevated in those diabetics. Schaper, N. C. *ACTA Endocrinol. (Copenh)* 122:7 (1990). Elevated GH in IDDM is thought to play an important role in diabetic complications, especially proliferative retinopathy. Holly, J. M. P. et al., *J. Endocr.* 118:353 (1988). Thus, GH suppression is a likely strategy to treat IDDM. Shumak, S. T. et al., *Clin. Invest. Med*, 13:287 (1990); Alzaid, A. A. et al., *Diabetes Care* 17:531 (1994).

In contrast to IDDM patients with little or no insulin secretion, non-insulin dependent diabetics (NIDDM) that are obese as well as non-diabetic obese individuals have elevated circulating insulin associated with depressed GH values. Meistas, M. T. et al., *Metabolism* 31:1224, (1982). Because insulin promotes storage of fuel as adipose and glycogen and that GH counters this action, low GH levels observed in obesity contribute further to development of adiposity. Thus, it would be desirable to treat obese individuals with GH or an agent that physiologically elevates GH. However, as described above, GH therapy has been demonstrated to counter insulin actions and therefore is contraindicated for individuals with diabetes or for those who are at risk for diabetes. Never-the-less, there have been several trials to examine GH therapy in obese individuals. Gertner, J. M. *Horm. Res.* 40:10 (1993). Data is far from convincing that such treatment promotes significant loss of fat tissue and there is no data that examined either insulin secretion or insulin sensitivity.

An alternative therapy to GH is to stimulate endogenous GH release by GH-releasing hormone (GHRH). Indeed, some consider this a more physiological approach. Both GHRH and a combination of GHRH with GH-Releasing peptides (GHRPs) have been tested in obese individuals. These studies demonstrated that the GH response to secretagogue is blunted in obesity. Kopelman, P. G. et al., *J. Clin. Endocrinol.* 23:87, (1985); Csizmadi, I. et al., *Metab.* 38:1016, (1989); DeMarinis, L. et al., *J. Clin. Endocrinol. Metab.* 74:1253, (1992); Cordido, F. et al., *J. Clin. Endocrinol. Metab.* 76:819 (1992); and Ghigo, E. et al., *Horm. Metab. Res.* 25:305 (1993). Since the intent of these studies was to test pituitary responsiveness to GH secretagogues in obesity and not to treat the pathophysiologic state, the pituitary challenge was acute and there were no attempts to measure insulin sensitivity or pancreatic insulin reserve.

Chronic combined administration of GHRH and GH-releasing hexapeptide has been studied in obese Zucker rats. Bercu, B. B. et al., *Endocrinology* 131:2800 (1992). The data indicate that the treated obese rats had similar body composition and plasma insulin values as vehicle treated obese counter parts. Additionally, the treated group appeared to tolerate an interperitoneal glucose injection better than untreated obese animals.

Prior to the present invention, GHRH had not been examined in animal models of NIDDM. Most unexpectedly, when GHRH or a functional analog thereof is administered to a diabetic mammal during the period of insulin resistance but prior to β-cell failure, insulin sensitivity as well as insulin secretion is enhanced. Islet cell failure is spared.

Accordingly, the present invention discloses a new, effective therapy for treating mammals afflicted with Non-insulin Dependent Diabetes (NIDDM) and other insulin resistant states such as those associated with obesity and aging. This therapy is contrary to conventional understanding of the diabetogenic properties of GH.

SUMMARY OF INVENTION

The present invention provides a method of treating an insulin resistant mammal, which comprises administering to a mammal in need thereof a growth hormone-releasing agent. More particularly, the present invention provides a method of treating mammals afflicted with non-insulin dependent diabetes mellitus.

DETAILED DESCRIPTION

Insulin resistant mammals includes mammals suffering from non-insulin dependent diabetes mellitus (NIDDM) or pre-NIDDM and other insulin resistant states such as glucose intolerance and those observed in aging and obesity. Most preferably, the present invention is practiced in those patients who are afflicted with insulin resistance, but have not experience β-cell failure.

A growth hormone releasing agent is a compound, that promotes the release and synthesis of growth hormone from the pituitary gland. Such agents include, for example, native growth hormone-releasing hormone (GHRH), analogs of GHRH, and agonists of the GHRH receptor. A growth hormone releasing agent may be a protein or a small organic compound. Growth hormone releasing agents include pharmaceutically acceptable salts thereof.

GHRH is known in the art as somatocrinin, Growth hormone Releasing Factor (GRF), and Growth Releasing Hormone (GRH). The primary structure of human GHRH is a polypeptide of the Formula (I): Unless otherwise indicated, amino acids are in the L configuration.

```
Tyr Ala Asp Ala Ile Phe Thr Asn Ser Tyr Arg Lys Val Leu   (SEQ ID NO:1)

Gly Gln Leu Ser Ala Arg Lys Leu Leu Gln Asp Ile Met Ser

Arg Gln Gln Gly Glu Ser Asn Gln Glu Arg Gly Ala Arg Ala

Arg Leu-NH2
```

One of ordinary skill in the art would appreciate that fragments of GHRH, preferably the N-terminal 29 residues, result in fully active forms of the protein. Likewise, chemical modifications, preferably to the C-terminal, result in fully active forms of the protein. These modifications to the native GHRH are referred to herein as functional analogs. Functional analogs of GHRH include, for example, analogs described in U.S. Pat. Nos. 4,517,181, 4,518,586, 4,528,190, 4,529,595, 4,563,352, 4,585,756, 4,595,676, 4,605,643, 4,620,976, 4,626,523, 4,628,043, and 4,689,318. Other functional analogs include those of Formula (I) wherein Ala at position 2 is substituted with Ile, Val, Thr, or Gly.

A number of additional functional analogs have been prepared to form longer lasting and/or more potent GHRH analogs, for example, D-amino acid residues in various regions of the GRF molecules are described in Lance, V. A., at al. *Biochem. Biophys. Res. Commun.* 119 265 (1984); Coy, D. H., et al. *Peptides* 8(suppl. 1), 49 (1986)). Peptide bond isoteres are incorporated in the N-terminal region, as described in Tourwe, D. *Janssen. Chim. Acta* 3,3 (1985); Hocart, S. J., et al. *J. Med.Chem.* 33, 1954–58 (1990). Other active functional analogs of GHRH include those described in *Biochemical and Biophysical Research Communications*, 123:2, 854–861 (1984); *Biochemical and Biophysical Research Communications*, 122:1, 304–310 (1984); *Biochemical and Biophysical Research Communications*, 139:2, 763–770 (1986); *Journal of Medicinal Chemistry*, 30:1, 219–222 (1987); *Peptide Research*, 1:1 36–41 (1988); *J. Med. Chem.*, 33, 1954–1958 (1990); *Horm. Metab. Res.*, 23, 15–21 (1991); *European Journal of Pharmacology*, 204, 179–185 (1991); *Int. J. Peptide Protein Res.*, 37, 14–20 (1991); *Peptide Research*, 5:4, 190–193 (1992); *J. Med. Chem.*, 35, 3928–3933 (1992); *Biochimica et Biophysica*, 1122, 147–153 (1992); *Int. J. Peptide Protein Res.*, 39 364–374 (1992); *J. Endocrinol. Invest.*, 16, 793–798 (1993), *J. Med. Chem.*, 36, 888–897 (1993); *Biopolymers* (*Peptide Science*), 37, 67–88 (1995); and *Proc. Natl. Acad. Sci.*, 92, 4872–4876 (1995).

Particularly preferred functional analogs of GHRH include those analogs described in European Patent Publication No. EP 511 003, hereinafter Formula II:

```
X1-Ala-Asp-Ala-Ile-Phe-Thr-A8-A9-Tyr-Arg-Lys-Val-Leu-A15-Gln-   (SEQ ID NO:2)

Leu-Ser-Ala-Arg-Lys-A22-Leu-Gln-A25-Ile-A27-Ser-Arg-Y-Z-T
``` wherein:
A8=Asn, Ala, Leu, Ser, or Thr;
A9=Ser, Ala, Leu, Thr, or Asn;
A15=Gly, Ala, Thr, or Leu;
A22=Ala or Leu;
A25=Asp or Glu;
A27=Met, Leu, or Norleucine;
Y=absent, or an amino acid sequence from 1 to 15 amino acids;
Z=absent, or an amino acid sequence of from 1 to 32 amino acids;
T=a carboxyl terminal group represented by the formula —COOR$_a$, —CR$_a$O, —CONHNHR$_a$, —CON(R$_a$)(R$_b$) or CH$_2$OR$_a$ wherein R$_a$ and R$_b$ independently are lower alkyl, hydrogen;
X1 is an acyl group represented by the formula

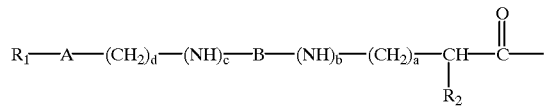

wherein
R$_1$=hydrogen, methyl, ethyl, hydroxyethyl, phenyl, or phenyl substituted by halo, lower alkyl, lower alkoxy, hydroxy, nitro, amino, acetamido, trifluoromethyl, —CH$_2$—OH, or sulfamido; or a 5 or 6 membered heterocycle containing one or more of N, O, or S;
a=zero, 1, 2, or 3;
b=zero or 1;
c=zero or 1;
d=zero to 12;
R$_2$=H, CH$_3$, CH$_2$OH, p-hydroxybenzyl, or

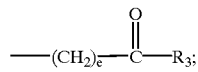

e=zero to 5;
A=absent, O or S;
B=carbonyl, sulfonyl and sulfinyl;
R$_3$=methyl, ethyl, hydroxyethyl, amino, hydroxyl, phenyl, or phenyl substituted with halo, alkyl, alkoxy, hydroxy, nitro, amino, acetamido, or sulfamido, or a 5 or 6 member heterocycle containing one or more of N, O, or S;
or a pharmaceutically acceptable salt thereof.

Preferred GHRH analogs are those wherein X1 is

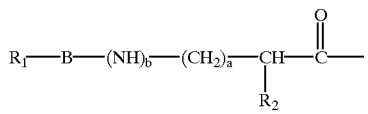

wherein
$R_1$=phenyl or phenyl substituted by halo, lower alkyl hydroxy, nitro, or amino;
a=0, 1 or 2;
b=1;
$R_2$=H; and
B=carbonyl.

Examples of groups represented by X1 of Formula II include p-chloro hippuroyl, p-methyl hippuroyl, p-nitro hippuroyl, hippuroyl, p-hydroxy hippuroyl, 3benzoyl propionyl, n-phthaloyl glycyl, N-phenylmalonamidoyl, p-methyl-N-phenylmalonamidoyl, or p-fluorohippuroyl.

In the definition of Formula II, the term "lower alkyl" refers to $C_1$–$C_4$ alkyl groups such as methyl, ethyl, n-propyl, isopropyl, n-butyl, sec-butyl, isobutyl and t-butyl; "lower alkoxy" refers groups such as methoxy, ethoxy, n-propoxy, t-butoxy and the like; "halo" refers to groups such as fluorine, chlorine, bromine and iodine; "substituted phenyl" refers groups such as phenyl substituted by one or two of the same or different groups selected from halo, lower alkyl, lower alkoxy, hydroxy, nitro, amino, acetamido or sulfonamido, exemplified by such groups as 4-chlorophenyl 3-iodophenyl, 2-fluorophenyl, 4-methylphenyl, 3 chloro-4-methylphenyl, 3-bromophenyl, 4-ethylphenyl, 3-ethoxyphenyl, 2-methoxyphenyl, 4-isopropoxyphenyl, 4-hydroxyphenyl, 3,4-dihydroxyphenyl, 2,4-dihydroxyphenyl, 4-nitrophenyl, 3-aminophenyl, 3-chloro-4-hydroxyphenyl, 2-acetamidophenyl, 4-sulfonamidophenyl, 3,4-dimethoxyphenyl, 2-fluoro-4-aminophenyl, and the like; "a 5 or 6 membered heterocycle containing one or more of N, O, or S" refers to the 5 membered heterocycles such as for example, pyrrole, thiophene, furan, imidazole, oxazole oxadiazole, thiazole, 1,3,4,-thiodiazole, asoxazole, and the like; and to 6-membered heterocycles such as for example, pyridine, pyrimidine, pyran, dihydropyran, thiazine, thiapyram, triazine and like 6-membered heterocycles. Such 5- and 6-membered heterocyles may also bear a substituent group such as lower alkyl, lower alkoxy, hydroxy, amino, or halo.

The designation "A20", "A21", etc., in reference to amino acid residues of the compound of Formula II, corresponds to the number of the particular amino acid when numbered consecutively from the amino terminus of the protein as it occurs in nature and in the literature. Such uniform numbering of amino acid residues of well characterized proteins is well known by those of ordinary skill in the art. Designations such as "des-Tyr-GHRH" are widely understood in the art as meaning the natural GHRH molecule lacking the amino-terminal tyrosine residue. Renumbering the remaining amino acid residues of the protein is unnecessary and may result in confusion. In the above example, it is understood that the amino acid occupying the second position in the naturally occurring protein would be the amino terminal residue but retain its designation as Ala2 for example. Similarly, Leu(27) hGHRH is understood by one of ordinary skill in the art as being human GHRH with position 27 substituted with Leu. Designations according to the well accepted amino acid designations of the different GHRH species will be followed herein.

Preferred peptides of the invention comprise compounds of the Formula II wherein Y is the 30–44 amino acid sequence of mature GHRH. Thus, preferred compounds of the invention comprise a compound of the Formula II wherein Y is the 30–44 amino acid sequence of the naturally occurring 30–44 amino acid sequence of the particular species of GHRH in question. An especially preferred Y peptide comprises the 30–43 amino acid sequence human GHRH.

Preferred peptides of the invention are represented when Z is absent or comprises the 45–76 amino acid sequence of the naturally occurring 45–76 amino acid sequence of the GHRH from the particular species under investigation. A most preferred form of the peptide moiety represented by Z comprises the naturally occurring 45–76 amino acid GHRH sequence of a particular species wherein the lysine residues thereof are replaced by arginine residues and the methionine residues are replaced by leucine residues. For example, an especially preferred GHRH analog exists when, Z comprises the amino acid sequence:

```
Gly-Arg-Gln-Val-Asp-Ser-Leu-Trp-Ala-Asp-Gln-Arg-Gln-Leu-  (SEQ ID NO:3)

Ala-Leu-Glu-Ser-Ile-Leu-Ala-Thr-Leu-Leu-Gln-Glu-His-Arg-

Asn-Ser-Gln-Gly.
```

A further preferred amino acid sequence of Z comprises the amino acid sequence:

```
Gly-Arg-Gln-Val-Asp-Gly-Val-Trp-Thr-Asp-Gln-Gln-Gln-Leu-  (SEQ ID NO:4)

Ala-Leu-Glu-Ser-Thr-Leu-Val-Ser-Leu-Leu-Gln-Glu-Arg-Arg-

Asn-Ser-Gln-Gly.
```

Preferred compounds of the invention comprise compounds of Formula II wherein the Y and/or Z peptides are of a sufficient length such that high level expression in *E. Coli* is achieved.

Preferred compounds of the invention further comprise GHRH analogs where none, one, or more than one of the amino acids having a free amino group is chemically modified. For purposes of the present invention, "chemically modified" is defined as the derivitization of an amino acid's free amino group with an alkyl or hydroxyalkyl group. The extent of modification is controlled by the length of reaction or the amount of reagent. It is preferred that all amino acids having a free amino group are chemically modified. Especially preferred is a GHRH which only has one free amino group that can be chemically modified. Such a compound has no lysine or methionine residues. Lysine and/or methionine-containing compounds are converted to compounds with a free amino group only at the N-terminus by replacing lysines with arginines and methionines with leucines.

The analogs of Formula II are prepared by methods well known in the art and described in European Patent Publication No. EP 511 003.

Growth hormone is known to be diabetogenic. Therefore, one skilled in the art world expect that stimulation of the GHRH receptor would exasperate the diabetic state. Therefore, it is most unexpected that treating insulin resistant patients with GHRH receptor agonists effectively treats insulin resistance. This unexpected activity is demonstrated, in vivo, in a Zucker Diabetic Fatty male rat (ZDF male rat assay) and in vivo, in an aged rat study.

Treating, as used herein, describes the management and care of a patient for the purpose of combating the disease, condition, or disorder and includes the administration of a compound of present invention to prevent the onset of the symptoms or complications, alleviating the symptoms or complications, or eliminating the disease, condition, or disorder. Treating an insulin resistant mammal includes increasing insulin sensitivity and/or insulin secretion to prevent islet cell failure.

The instant invention further provides pharmaceutical formulations and medicaments comprising compounds useful in the present invention. The proteins, preferably in the form of a pharmaceutically acceptable salt, can be formulated for parenteral administration for the therapeutic or prophylactic treatment of NIDDM. For example, compounds of the Formula (II) can be admixed with conventional pharmaceutical carriers and excipients. These compositions comprise proteins containing from about 0.1 to 90% by weight of the active protein, preferably in a soluble form, and more generally from about 10 to 30%. Furthermore, the present proteins may be administered alone or in combination with other agents. For intravenous (iv) use, the protein is administered in a commonly used intravenous fluid and administered by infusion. Such fluids, for example, physiological saline or Ringer's solution can be used.

For intramuscular preparations, a sterile formulation, preferably a suitable soluble salt form of a protein of the Formula (I) or (II), for example the hydrochloride salt, can be dissolved and administered in a pharmaceutical diluent such as pyrogen-free water (distilled) or physiological saline. A suitable insoluble form of the compound may be prepared and administered as a suspension in an aqueous base or a pharmaceutically acceptable oil base, e.g. an ester of a long chain fatty acid such as ethyl oleate. Pharmaceutically acceptable preservatives such as an alkylparaben, particularly methylparaben, propylparaben, or butylparaben or chlorobutanol are preferably added to the formulation to allow multi-dose use. The formulation is preferably prepared in the absence of salt to minimize the ionic strength of the formulation.

A pharmaceutically effective dosage is an amount necessary to stimulate the GHRH receptor. The dosages administered to an insulin resistant mammal will be determined by the physician in the light of the relevant circumstances including the choice of growth hormone releasing agent administered, the condition of the mammal, and the chosen route of administration. The dosage ranges presented herein as well as the Examples are not intended to limit the scope of the invention in any way.

EXAMPLE 1

ZDF Male Rat Assay

A growth hormone releasing agent is continuously administered to Zucker diabetic male rats subcutaneously by use of an "Alzet" mini osmotic pump. The treatment was started at approximately 6 weeks of age and continued for approximately 6–8 weeks. The experiment was designed to allow the study of changes in the typical plasma glucose and insulin level profiles with the progression of the diabetic disease state.

Methods:

Zucker Diabetic Fatty (ZDF/Gmi™-fa/fa) male rats were obtained from Genetic Models Inc. (Indianapolis, Ind.). The rats were maintained on Purina Formula 5008 rat chow (Purina Mills, Inc., St. Louis, Mo.) and housed in a light controlled room of alternating 12 hour cycles of light and dark. Rats were singly housed and given free access to food and water. At 5 weeks of age, an oral glucose tolerance test (OGTT: 16 hr fast, oral glucose concentration at 2.5 grams/kg body weight; Butler dextrose solution 50%, lot # 3342, Ft. Collins, Colo.; time points at 0, 30, 60, and 120 minutes) was given to each rat and their plasma assayed for glucose and insulin levels. At 6 weeks of age Alzet minipumps, containing a 1.5 inch polyethylene tube extensions (Model 2001, lot # 040401, 1.0 µl/hr, 7 days; Alza Corporation, Palo Alto, Calif.) were implanted subcutaneously. Animals were anesthetized with isoflurane at approximately 2–3% in oxygen. Each rat was shaved and a Povidone Iodine scrub was used at the site of implantation. A small incision was made above and just posterior to the shoulder. A small pocket was made and the pump placed in so the delivery port was away from the incision. The incision was then closed with wound clips and the rat observed and kept warm until awake. At the end of 7 days the pumps were removed from the rat and a new pump implanted subcutaneously as previously described. Pumps contained vehicle (PBS) or a growth hormone releasing agent (8 rats/group).

The GH releasing agent was prepared at concentrations of 625 and 62.5 µg/mL and loaded into Alzet pumps using sterile techniques. Body weight and food consumption were monitored once a week. Rats were bled from the tail for plasma glucose, insulin, and growth hormone levels weekly. One week prior to sacrificing the rats, an I.P. injection of tetracycline was given to each rat and then again the day before sacrificing (20 mg/mL; 0.5 mL/animal) to determine bone growth.

Assays: Plasma glucose concentrations were determined by the glucose hexokinase method (IL Test GLucose, lot # I1040502; Instrumentation Laboratory Company, Lexington, Mass.) with a model 2000 Monarch (Instrumentation Laboratory Company, Lexington, Mass.). Insulin was determined with a Coat-a-Count kit (Diagnostic Products Corporation, Los Angeles, Calif.) using a rat insulin standard (Lilly Research Laboratories, Indianapolis, Ind.). Glucagon was assayed with a double antibody procedure using guinea pig anti-glucagon (Catalog no. 1032; Linco Research, St. Louis, Mo.), goat anti-guinea pig (lot # T67-7GZ-237); Lilly Research Laboratories, Indianapolis, Ind.) and $^{125}$I-glucagon (DuPont New England Nuclear, Wilmington, Del.). Growth hormone was assayed using rat growth hormone standard (purchased from Parlow, Torrance Calif.; rGH-RP-2, lot AFP-3190B), anti rGH (purchased from Parlow, Torrance Calif.; rGH-s-r, lot AFP411S), $^{125}$I-rGH (Corning-Hazelton, Vienna, Va.) and protein A IGSL100 (Enzyme Center, Malden, Mass.).

EXAMPLE 2

Aged Rat Study

Animals: Male Fischer 344 rats 26 months of age were randomly assigned to three treatment groups (8 animals per group). Animals were housed in individual cages in a temperature and humidity-controlled environment and exposed to 12 h light/12 h dark lighting schedule (lights on at 0600 h). Animals were fed ad libitum on a daily basis.

Treatments: Animals received daily injection (sc., 0.5 ml at 0700 h) of vehicle; active compound, 2 µg/kg body weight for six weeks. At the end of the treatment period and one day prior to testing, food was removed and animals were fasted for 16 hours. Glucose tolerance test was initiated at 0700 h in conscious and freely moving rats. Blood was collected by tail clipping method. A control blood sample (0.2 mL) was collected before ingesting glucose (2.5 g/kg body weight). Subsequent blood samples were collected at 30, 60, 90 and 120 min. after glucose ingestion. Blood was collected on ice and glucose concentrations were determined by bichromatic analysis using the IL Monarch Chemistry Systems (Cat. # 35199, Instrumentation Laboratory, Mass.). Plasma was separated and samples were kept frozen (−20° C.) until assay for insulin concentrations using double antibody radioimmuonoassay.

Young Fischer 344 rats (2 months of age) were purchased (Harlan, Ind.). Animals were housed for 2 weeks under the same conditions as described earlier. Glucose tolerance test was conducted as described and glucose and insulin concentrations were evaluated.

Area under the response curve was calculated using the trapezoidal method and data were analyzed by ANOVA with Duncan's multiple range test.

A functional analog of GHRH, p-methyl hippuroyl Leu (27) (1-44)OH hGHRH, disclosed in European Patent Publication No. EP 511 003 and known to be an agent capable of stimulating growth hormone release and representative of the activity of GHRH or a functional analog thereof, was evaluated in the ZDF Male rat assay and the aged rat assay. The results are demonstrated in Tables 1 through 3.

TABLE 1

Final Body Weight and Composition in ZDF Rats Infused with a Funtional GHRH Analog from 6-Weeks of Age to 14-Weeks of Age

| Weight (g) | Control | 0.001 µg/min | 0.01 µg/min |
|---|---|---|---|
| Total Body Mass | 340.58 | 327.06 | 388.16* |
| Lean Mass | 340.58 | 327.06 | 388.16* |
| Liver | 22.12 | 22.21 | 24.79 |
| Spleen | 0.83 | 0.8 | 1.18 |
| Epididymal Fat | 0.26 | 0.25 | 0.33 |
| Heart | 1.52 | 1.44 | 1.69 |
| Thymus | 0.81 | 0.86 | 0.99 |

[1]Analog infusion was started at 6 weeks of age and was maintained until 14 weeks of age. Values are the mean of 8 individual animals.
*Denotes statistically significant (p < 0.05).

TABLE 2

Mean Plasma Glucose and Plasma Insulin Levels During Continuous Infusion of Functional Analog[1]

| AGE (weeks) | Control | 0.001 µg/min | 0.01 µg/min |
|---|---|---|---|
| | Plasma Glucose (mg/dl) | | |
| 6 | 140.51 | 139.99 | 139.86 |
| 7 | 157.31 | 155.34 | 148.68 |
| 8 | 204.24 | 183.41 | 165.01 |
| 9 | 299.18 | 331.91 | 215.49 |
| 10 | 359.68 | 389.18 | 235.91 |
| 11 | 410.40 | 392.65 | 232.89* |
| 12 | 454.40 | 496.75 | 317.11* |

TABLE 2-continued

Mean Plasma Glucose and Plasma Insulin Levels During Continuous Infusion of Functional Analog[1]

| AGE (weeks) | Control | 0.001 µg/min | 0.01 µg/min |
|---|---|---|---|
| 13 | 458.41 | 446.03 | 248.28* |
| 14 | 484.47 | 461.40 | 229.36* |
| | Plasma Insulin (ng/ml) | | |
| 6 | 10.90 | 9.81 | 11.21 |
| 7 | 22.76 | 23.91 | 24.76 |
| 8 | 27.42 | 27.33 | 26.81 |
| 9 | 24.37 | 21.11 | 24.23 |
| 10 | 23.20 | 20.18 | 27.85 |
| 11 | 20.60 | 20.98 | 30.05* |
| 12 | 19.84 | 21.48 | 36.45* |
| 13 | 18.41 | 16.29 | 29.92* |

[1]GHRH analog infusion was started at 6 weeks of age and was maintained until 14 weeks of age. Values are the mean of 8 individual animals.
*Denotes statistically significant (p < 0.05).

TABLE 3

Oral Glucose Tolerance in Aged Rats is Improved by Daily Treatment with GHRH Analog

| Time (min) | Young | Aged Control | Aged GHRH |
|---|---|---|---|
| | Plasma Glucose (mg/dL) | | |
| 0 | 104.4 | 110.7 | 104.2 |
| 30 | 116.4 | 160.1 | 148.4 |
| 60 | 124.7 | 151.3 | 154.8 |
| 120 | 94 | 147.8 | 148.1 |
| AUC (mg. min/dL) | 13,483.20 | 17,705.70 | 16,833.80 |
| | Plasma Insulin (ng/mL) | | |
| 0 | 2.00 | 1.23 | 1.26 |
| 30 | 1.71 | 1.33 | 1.64 |
| 60 | 2.86 | 1.51 | 1.92 |
| 120 | 2.32 | 1.24 | 1.41 |
| AUC (ng.min/mL) | 278.84 | 163.74 | 196.25* |

[1]Aged (26-month old) Fisher 344 rats were injected with GHRH analog (2 µg/kg) daily for 6 weeks. For comparison, data obtained from young (2 month old) untreated Fisher 344 rats is included. AUC is the area under the plasma glucose- and plasma insulin- vs. time curves.
*Denotes values are significantly different than that observed in aged control animals.

The data of Tables 1 through 3 demonstrate that including growth hormone release causes an improvement in giycemic control, increased insulin sensitivity, and increased insulinlin secretion. Thus, the administration of a growth hormone releasing agent is an effective therapy for NIDDM and other insulin resistance states.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A method of treating insulin resistance in mammals, which comprises administering to a mammal in need thereof a growth hormone releasing agent or a pharmaceutical acceptable salt thereof.

2. A method of claim 1 wherein the mammal is a non-insulin dependent diabetic mammal.

3. A method of claim 1 wherein the mammal is a non-insulin dependent diabetic human.

4. A method of claim 3 wherein the growth hormone releasing agent is selected from the group consisting of growth hormone releasing hormone, a funtional analog of growth hormone releasing hormone, or a pharmaceutically acceptable salt of the foregoing.

5. A method of claim 3 wherein the growth hormone releasing agent is a compound of the formula:

X1-A2-Asp-Ala-Ile-Phe-Thr-A8-A9-Tyr-Arg-Lys-Val-   (SEQ ID NO:2)

Leu-A15-Gln-Leu-Ser-Ala-Arg-Lys-A22-Leu-Gln-A25-

Ile-A27-Ser-Arg-Y-Z-T wherein:
A2=Ile, Val, Thr, or Gly
A8=Asn, Ala, Leu, Ser, or Thr;
A9=Ser, Ala, Leu, Thr, or Asn;
A15=Gly, Ala, Thr, or Leu;
A22=Ala or Leu;
A25=Asp or Glu;
A27=Met, Leu, or Norleucine;
Y=absent, or an amino acid sequence from 1 to 15 amino acids;
Z=absent, or an amino acid sequence of from 1 to 32 amino acids;
T=a carboxyl terminal group represented by the formula —COOR$_a$, —CR$_a$O, —CONHNHR$_a$, —CON(R$_a$)(R$_b$) or CH$_2$OR$_a$ wherein R$_a$ and R$_b$ independently are lower alkyl, hydrogen;
X1 is an acyl group represented by the formula

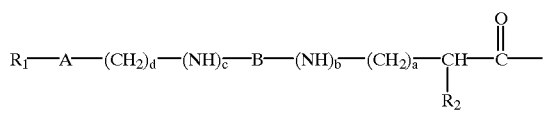

wherein
R$_l$=hydrogen, methyl, ethyl, hydroxyethyl, phenyl, or phenyl substituted by halo, lower alkyl, lower alkoxy, hydroxy, nitro, amino, acetamido, trifluoromethyl, —CH$_2$—OH, or sulfamido; or a 5 or 6 membered heterocycle containing one or more of N, O, or S;
a=zero, 1, 2, or 3;
b=zero or 1;
c=zero or 1;
d=zero to 12;
R$_2$=H, CH$_3$, CH$_2$OH, p-hydroxybenzyl, or

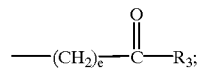

e=zero to 5;
A=absent, O or S;
B=carbonyl, sulfonyl and sulfinyl;
R$_3$ =methyl, ethyl, hydroxyethyl, amino, hydroxyl, phenyl, or phenyl substituted with halo, alkyl, alkoxy, hydroxy, nitro, amino, acetamido, or sulfamido, or a 5 or 6 member heterocycle containing one or more of N, O, or S;

or a pharmaceutically acceptable salt thereof.

6. A method of claim 5 wherein X1 is

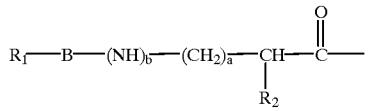

wherein
R$_l$ =phenyl or phenyl substituted by halo, lower alkyl hydroxy, nitro, or amino;
a=0, 1 or 2;
b=1;
R$_2$=H; and
B=carbonyl.

7. A method of claim 5 wherein X1 is selected from the group consisting of p-chloro hippuroyl, p-methyl hippuroyl, p-nitro hippuroyl, hippuroyl, p-hydroxy hippuroyl, 3-benzoyl propionyl, n-phthaloyl glycyl, N-phenylmalonamidoyl, p-methyl-N-phenylmalonamidoyl, or p-fluorohippuroyl.

8. A method of claim 5 wherein X1 is selected from the group consisting of p-methyl hippuroyl or hippuroyl.

9. A method of claim 5 wherein Y is the 30–44 amino acid sequence of mature growth hormone releasing hormone .

10. A method of claim 5 wherein z is selected from the group consisting of SEQ ID NO:3 or 4.

11. A method of claim 5 wherein T is selected from the group consisting of —COOR$_a$, —CR$_a$O, —CONHNHR$_a$, —CON(R$_a$) (R$_b$) or CH$_2$OR$_a$ and wherein R$_a$ and R$_b$ independently are lower alkyl or hydrogen.

12. A method of claim 5 wherein A2 is Val, A8 is Asn, A9 is Ser, A15 is Gly, A22 is Leu, A25 is Asp, A27 is Met.

13. A method of claim 5 wherein A2 is Ala, A8 is Asn, A9 is Ser, A15 is Gly, A22 is Leu, A25 is Asp, A27 is Met.

14. A method of claim 8 wherein A2 is Ala, A8 is Asn, A9 is Ser, A15 is Gly, A22 is Leu, A25 is Asp, A27 is Met.

15. A method of claim 8 wherein A2 is Val, A8 is Asn, A9 is Ser, A15 is Gly, A22 is Leu, A25 is Asp, A27 is Met.

16. A method claim 5 wherein X1 is selected from the group consisting of p-methyl hippuroyl or hippuroyl, A2 is Ala, A8 is Asn, A9 is Ser, A15 is Gly, A22 is Leu, A25 is Asp, A27 is Met, Y is the 30–44 amino acid sequence of mature GHRH, Z is the 45–76 amino acid sequence of mature GHRH, and T is —COOR$_a$, —CR$_a$O, —CONHNHR$_a$, —CON(R$_a$)(R$_b$) or CH$_2$OR$_a$ wherein R$_a$ and R$_b$ independently are lower alkyl or hydrogen.

17. A method of claim 5 wherein X1 is p-methyl hippuroyl, A2 is Ala, A8 is Asn, A9 is Ser, A15 is Gly, A22 is Leu, A25 is Asp, A27 is Met, Y is the 30–44 amino acid sequence of mature human growth hormone releasing hormone, Z is the 45–76 amino acid sequence of mature human growth hormone releasing hormone, and T is —COOH.

18. A method of claim 5 wherein X1 is hippuroyl, A2 is Ala, A8 is Asn, A9 is Ser, A15 is Gly, A22 is Leu, A25 is Asp, A27 is Met, Y is the 30–44 amino acid sequence of mature human growth hormone releasing hormone, Z is the 45–76 amino acid sequence of mature human growth hormone releasing hormone, and T is —COOH.

19. A method of claim 5 wherein X1 is p-methyl hippuroyl, A2 is Val, A8 is Asn, A9 is Ser, A15 is Gly, A22 is Leu, A25 is Asp, A27 is Met, Y is the 30–44 amino acid sequence of mature human growth hormone releasing hormone, Z is the 45–76 amino acid sequence of mature human growth hormone releasing hormone, and T is —COOH.

20. A method of claim 5 wherein X1 is hippuroyl, A2 is Val, A8 is Asn, A9 is Ser, A15 is Gly, A22 is Leu, A25 is Asp, A27 is Met, Y is the 30–44 amino acid sequence of mature human growth hormone releasing hormone, Z is the 45–76 amino acid sequence of mature human growth hormone releasing hormone, and T is —COOH.

21. A method of treating impaired glucose tolerance which comprises administering to a mammal in need thereof a growth hormone releasing agent or a pharmaceutically acceptable salt thereof.

22. A method of claim 21 wherein the mammal is a human with a high risk for non insulin dependent diabetes.

* * * * *